United States Patent [19]

Cirelli et al.

[11] Patent Number: 4,886,499
[45] Date of Patent: Dec. 12, 1989

[54] PORTABLE INJECTION APPLIANCE

[75] Inventors: Giorgio Cirelli, Nussbaumen; Hans Steffen, Liestal, both of Switzerland; Christian Surber, San Francisco, Calif.

[73] Assignee: Hoffmann-La Roche Inc., Nutley, N.J.

[21] Appl. No.: 129,018

[22] Filed: Dec. 4, 1987

[30] Foreign Application Priority Data

Dec. 18, 1986 [CH] Switzerland .......................... 5021/86

[51] Int. Cl.$^4$ .............................................. A61M 5/14
[52] U.S. Cl. ..................................... 604/131; 604/141; 604/145; 604/153; 128/DIG. 12
[58] Field of Search ............... 604/131, 136, 138, 141, 604/142, 145, 147, 153, 156, 157, 180, 896; 128/DIG. 12

[56] References Cited

U.S. PATENT DOCUMENTS

| | | | |
|---|---|---|---|
| 4,214,584 | 7/1980 | Smirnov et al. ................. | 604/157 X |
| 4,316,463 | 2/1982 | Schmitz et al. . | |
| 4,340,048 | 7/1982 | Eckenhoff . | |
| 4,483,666 | 11/1984 | Schubert et al. . | |
| 4,525,164 | 6/1985 | Loeb et al. . | |
| 4,552,561 | 11/1985 | Eckenhoff et al. ............. | 604/131 X |
| 4,601,707 | 7/1986 | Albisser et al. .................. | 604/131 |
| 4,626,244 | 12/1986 | Reinicke ............................. | 604/141 |
| 4,734,092 | 3/1988 | Millers ............................ | 604/151 X |
| 4,738,660 | 4/1988 | Lucas ............................. | 604/157 X |

FOREIGN PATENT DOCUMENTS

| | | |
|---|---|---|
| 87045/82 | 8/1982 | Australia . |
| 168675 | 1/1986 | European Pat. Off. . |
| 195637 | 9/1986 | European Pat. Off. . |
| 197625 | 10/1986 | European Pat. Off. . |

OTHER PUBLICATIONS

PCT WO 82/03556, 10–82.

Primary Examiner—Stephen C. Pellegrino
Attorney, Agent, or Firm—Jon S. Saxe; Bernard S. Leon; A. Kate Huffmann

[57] ABSTRACT

The portable appliance is of use for the subcutaneous or intradermal injection of a liquid formulation of an active principle and it comprises in combination: a supply vessel for the formulation; an injection needle adapted to communicate with the vessel; pump means for emptying the vessel through the injection needle; securing means for securing the appliance to an appropriate part of the patient's body; and needle-driving means for shooting the injection needle into the patient's skin.

37 Claims, 5 Drawing Sheets

PORTABLE INJECTION APPLIANCE

BACKGROUND

1. Field of the Invention

The invention relates to a portable appliance for the subcutaneous or intradermal injection of a liquid formulation of an active principle or ingredient.

2. Description

There has for some time past clearly been a need for small, compact and portable injection appliances which can be worn on a suitable part of the body and which provide a preferably subcutaneous release of accurately defined quantities of active principles into the body over prolonged periods of time. Various devices of this kind having considerable advantages over the conventional subcutaneous syringe are already known. In conventional subcutaneous injection a so-called bolus of an active principle is introduced into the body and must be gradually absorbed and distributed therein. Distribution depends to a considerable extent upon the physiological circumstances of the individual being treated and is therefore uncontrollable. The advantage of appliances which release an active principle continuously over a prolonged period of time is that administration can be accurately controlled to suit the body's requirements. Indeed, it is possible for phases of release to alternate with phases of non-release. A physiologically adapted release of this kind is advantageous more particularly in the case of highly active agents such as insulin, interferon or the like.

Conventionally, known appliances of this kind have a vessel which contains the active principle and with which an injection needle communicates. Pump means discharge the contents of the vessel into the body of a patient over a predetermined period of time. DE No. 3 121 888 (U.S. Pat. No. 4,601,707) discloses an example of such an appliance. It has a supply vessel in the form of a hose which a clockwork-driven squeezing roller empties through an injection needle connected to the end of the hose. The needle is introduced into the tissue some distance away from the appliance. The appliance can be worn or carried on the wrist like a wrist watch. An appliance of a different kind disclosed in U.S. Pat. No. 4,552,561 can be stuck to the skin and carries the injection needle on its underside so that the place where the needle penetrates the skin is covered while the appliance is in use. This appliance also needs the needle to pierce the tissue. It is more particularly the piercing of the tissue with the needle that is problematic in the case of conventional subcutaneous bolus injections and in the case of the more recent subcutaneous injection appliances hereinbefore described. People who are not experts in medicine are usually insufficiently practised to place such a needle correctly and they suffer from a completely justified fear of the likely pain.

SUMMARY OF THE INVENTION

The invention provides a portable injection appliance of the kind hereinbefore set out which is free from the disadvantages of the known appliances and which can readily be used more particularly by persons not expert in medicine. Illustratively, the inventive appliance permits a patient to inject himself automatically and receive long term and slow release of a formulation.

According to the invention, this is achieved by a portable injection appliance which is distinguished by a combination comprising: a supply vessel for retaining the formulation to be injected; an injection needle adapted to communicate with the vessel; pump means for emptying the vessel through the injection needle into the patient; securing means for securing the appliance to an appropriate part of the patient's body; and needle-driving means for shooting the injection needle into the patient's skin.

The appliance can also comprise flow control means enabling the release of the formulation of active principle either to be kept constant or to follow a predetermined profile of flow.

According to another feature of the invention, the appliance is divided in two parts, the part containing the more valuable elements can be reused while the other part can be discarded as an expendable item after being used once.

The vessel for the active principle or the solution thereof can quite simply be, for example, a part of the appliance casing, in which case an appropriate diaphragm (e.g., which is made of elastomers or metals or the like in single or multilayer form) delimits a chamber. Another possibility for a supply vessel is a closed vessel also made of elastomers or metals or the like, for example, in the form of bellows. The supply vessel can also take the form of a squeezable hose such as referred to by way of example in the Background section hereof. The vessel can also take the form of a plunger syringe whose cylinder is operative as a supply vessel. An absorbent material like a sponge can be used to take up the active principle. More than one separate supply vessel or chamber can be provided, for example, when two active principles have to be injected or when a lyophilisate of active principle and a reconstituting solvent are used. Various forms of energy can be considered for driving the vessel-emptying pump means. For instance, the pump can be gas-operated, in which event the pressure necessary to empty the vessel can be produced by electrolysis or photolysis or chemical reactions and by propellant vapours such as dichlodifluoromethane (Freon) or the like. Another possibility is to produce the requisite pressure by ordinary osmosis or electro-osmosis. Mechanical drives using, for example, springs or bimetallic elements or memory alloys or clockwork drives are of course another possibility. Electric or magnetic drives such as the known electric pumps, diaphragm pumps, piezoelectric pumps, electric clock drives or magnets can also be considered.

An adhesive layer on the patient-engaging surface of the appliance, such layer possibly extending as a plaster beyond the appliance, is more particularly suitable for securing the appliance to the appropriate part of the patient's body. A possible alternative is a securing band or tape like the armband shown in the German Offenlegungsschrift hereinbefore mentioned.

The needle-driving device is preferably a metal spring.

For constant flow operation the active principle is arranged to be released constantly, for example, by means of capillaries or frits or diaphragms. Also, the flow can be adjusted by adaptation of the viscosity of the liquid formulation of the active principle.

Control of the quantity of active principle released can also be embodied in various ways. For example, a squeezable hose whose diameter is increased or reduced to suit requirements can be disposed between the supply vessel and the needle. Another possibility is to provide a pressure-reducing valve. Another possibility is to select a particular range of the expansion of the driving spring or to use special cup springs in which the force is constant within limits over a distance. More elaborate flow control can be provided by feedback using sensors. Flow control can also be on the basis of a specially programmed pumping mechanism being used for the vessel-emptying operation.

Very thin capillaries—i.e., capillaries having a diameter of preferably <0.5 mm—are used as injection needles, since pain increases with needle diameter thickness. The depth of penetration and the way in which the needle is ground also have a bearing on pain. Advantageously, therefore, the penetration depth is at most 5,000 μm. Also, the needle is preferably ground at an inclination, for example, like a lancet.

Even when needle diameter and penetration depth do not cause pain, the formulation itself may cause pain or irritation. This can be countered by including a local anesthetic in the formulation.

PREFERRED EMBODIMENTS OF THE INVENTION

Embodiments of the invention will be described hereinafter with reference to the accompanying drawings wherein.

DETAILED DESCRIPTION OF THE INVENTION

Figure 1:
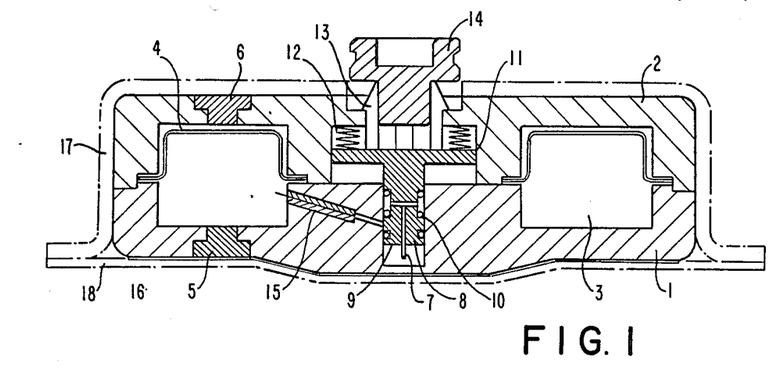
FIG. 1 is a cross-section (A—A) through an injection appliance according to the invention.
Figure 2:
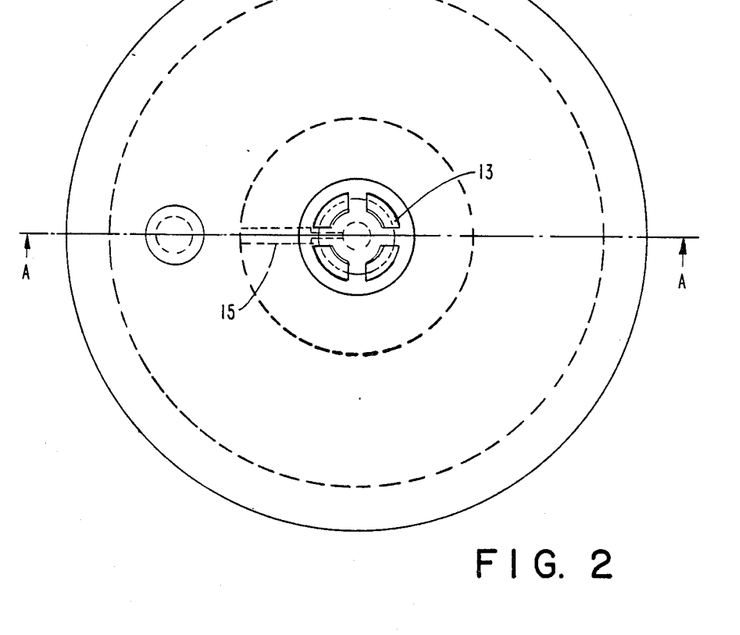
FIG. 2 is a plan view of the appliance shown in FIG. 1.

The inventive appliance shown in FIGS. 1 and 2 comprises a two-part flat cylindrical discoid casing having a bottom part 1 and a top part 2. The two parts 1, 2 are rididly and releasably interconnected, for example, by screwthreading (not shown). Annular recesses in the contacting surfaces of the two parts 1, 2 together form an annular chamber 3. A diaphragm 4 subdivides the same into two separate chambers, both of which communicate with the exterior by way of filling orifices 5, 6 normally closed by plugs.

An injection needle 7 and driving means for shooting the same into a patient's skin and injecting the principle therein are disposed at the center of the discoid casing. The needle is a steel capillary of 200 μm diameter. Alternatively, a glass capillary could be used. A carrier 8 retains and carries the needle 7. The carrier 8 has a bottom cylindrical part and a top flat discoid part. The cylindrical part is disposed for axial movement along the central axis of the appliance in a corresponding bore 9 in the casing bottom part 1 and is formed with a bore 10 which extends perpendicularly to its axis and which communicates with the interior of the needle 7. The cylindrical outside surface of the cylindrical part is formed with three peripheral grooves in which O-ring seals are introduced. There is also a shallow peripheral groove at the level of the bore 10.

In its bottom part at the outside wall of part 1, the bore 9 reduces to a diameter just large enough for the needle to pass through.

The top discoid part of the needle carrier 8 is disposed for axial movement in a corresponding further concentric bore 11 of the casing top part 2. Over substantially two-thirds of the thickness of the part 2 the bore 11 reduces to substantially half its diameter so that an abutment or shoulder is formed. Disposed between the same and the top part of the needle carrier 8 is a driving spring 12 for driving the needle 7 into the patient's skin (not shown) adjacent the bottom casing part 1.

The needle carrier 8 also has resilient retaining fingers 13 which extend upwards from its surface and which have a pawl-like step or shoulder engaging the edge of a widening of the bore 11. When the fingers 13 are in the engaged state the carrier 8 with the needle 7 is in its top position in which the spring 12 is under stress and the needle does not project beyond the casing bottom surface.

Disposed between the fingers 13 is a safety cover or cap 14 which in the position shown in the Figures has one side to prevent accidental compression of the fingers 13 likely to trigger the needle drive. When the patient is prepared to automatically inject the needle into the skin, the cover 14 is pulled from the appliance. The cover then is reversed and repositioned so that its previously free side now faces into and surrounds fingers 13. That is, the safety cover 14 is formed on its free side with a bore whose diameter is so adapted to approximate and mate with the inclined surfaces of the fingers 13 so that the same are pressed together when the cap 14 is again pressed onto the appliance. The retaining mechanism, thus, is released as the fingers 13 are pressed together.

A communicating bore 15 is disposed in the casing bottom part between the bottom compartment of the chamber 3 and the bore 9. The same widens over some of its length to receive a restrictor element, such as a Teflon frit. The bore 15 so extends as to join the bore 9 at a height corresponding to the bore 10 in the needle carrier 8 when the same is in its bottom position. In the top end position the opening where the bore 15 joins the bore 9 is closed by the cylindrical part of the needle carrier 8 and by the bottom two O-rings.

The appliance has an adhesive layer 16 on its underside. The appliance is also embedded in a correspondingly shaped securing plaster 17. The layer 16 and the adhesive layer of the plaster are protected before use by a foil 18. The adhesive layer 16 on the underside and the adhesive layer of the plaster can contain additional substances such as a local anesthetic.

In production, after the appliance has been assembled the bottom compartment of the chamber 3 is filled with a required active principle by way of the aperture 5, whereafter the same is closed. Also, the top compartment of the chamber 3 above diaphragm 4 is filled with a propellant through the aperture 6. These fillings are usually production operations and in that case are not carried out by the user. However, in the case of some active principles it may be convenient to carry out filling shortly before use. The appliance is then ready for use.

The appliance operates as follows:

The user removes the foil 18 and sticks the appliance at an appropriate part of his body by means of the plaster 17 and adhesive foil 16. The user then removes the safety cap 14, turns it and presses it onto the inclined surfaces of the fingers 13. The same are therefore compressed and release the needle drive. The spring 12 expands and presses the needle carrier 8 with the needle 7 downwards through the predetermined distance and through the adhesive foil onto the user's skin. The needle should penetrate something like at least 50 $\mu$m and at most approximately 5000 $\mu$m into the skin. The piercing of the skin by the needle is painless or nearly so because of the reduced depth of penetration, the small diameter of the needle and its inclined grinding.

Simultaneously as the needle carrier 8 descends the cross-bore 10 moves to the height of the opening of the communicating bore 15 so that the same communicates with the needle 7. The way is then open for the active principle to flow through the needle, the flow being determined by the pressure of the propellant in the top compartment of the chamber 3 and by the restriction provided by the restrictor 15. The volume of the flow of active principle and, therefore, the duration of injection can be determined by appropriate choice of these factors.

Figure 3:
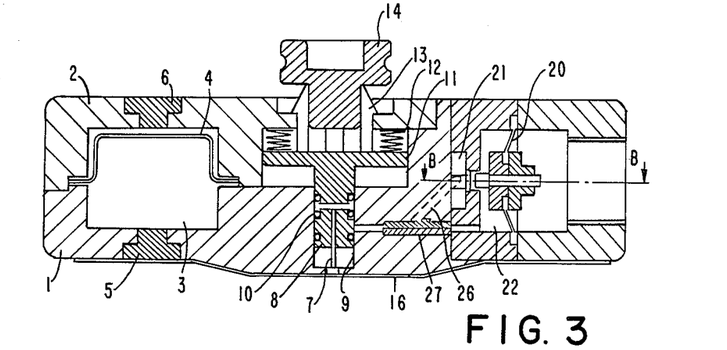
FIG. 3 is a cross-section (A—A) through another embodiment of the invention.
Figure 4:
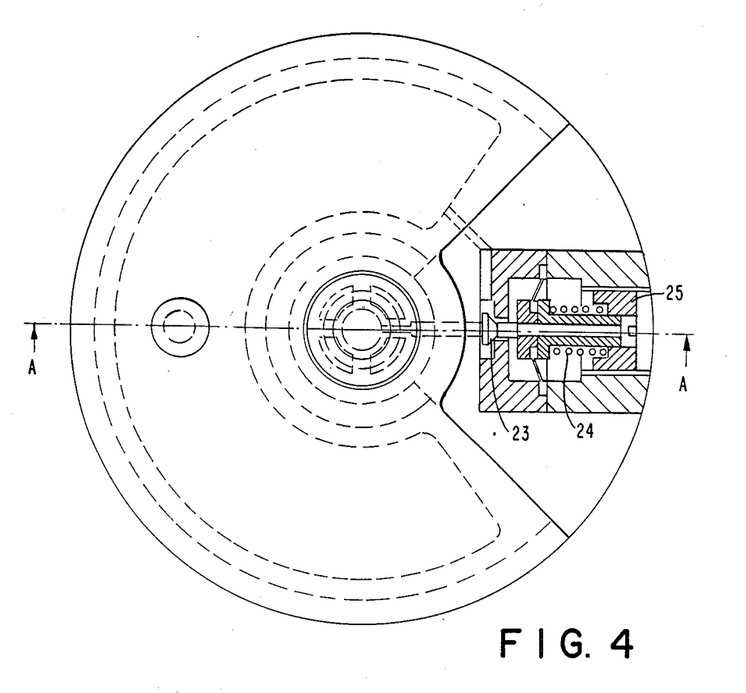
FIG. 4 is a plan view with partial sectioning of the appliance shown in FIG. 3.

The appliance shown in FIGS. 3 and 4 has the same storage vessel and the same needle-shooting device as the embodiment hereinbefore described. An additional feature, operative to compensate for variations in the pressure of the propellant is a pressure-reducing valve. The same is disposed in a segment of the circular casing. Correspondingly, the chamber 3 extends around only some of the periphery.

The reducing valve has its own casing which is received in a corresponding recess in the appliance casing. Internally the reducing valve is subdivided by a diaphragm 20, in a manner conventional in pressure-reducing valves, into a high-pressure chamber 21 and a low-pressure chamber 22. A ram 23 is disposed in the communicating bore between the chambers 21 and 22, is secured to the diaphragm 20 at its center and can close the communicating orifice by moving axially. A spring 24 is disposed on the other side of the diaphragm between the ram 23 and an adjustable abutment 25. The spring 24 basically determines the pressure in the low-pressure chamber. The high-pressure chamber 21 communicates by way of a communicating bore 26 with the bottom compartment of the chamber 3 - i.e., the reservoir of active principle. The low-pressure chamber 22 communicates by way of bore 27 with the central bore 9 and, as in the embodiment hereinbefore described, opens out at the level of the cross-bore 10 when the needle carrier 8 is in its bottom end position.

The pressure-reducing valve enables a substantially constant release rate of active principle to be maintained irrespective of pressure variations on the high-pressure side. Such pressure variations may be caused by variations in the vapour pressure of the propellant as a result of temperature variations.

As in the previous example, the appliance shown in FIGS. 3 and 4 also has an adhesive layer, a securing plaster 17 and a protective foil 18 and operates in virtually the same way as the embodiment previously described.

Figure 5:
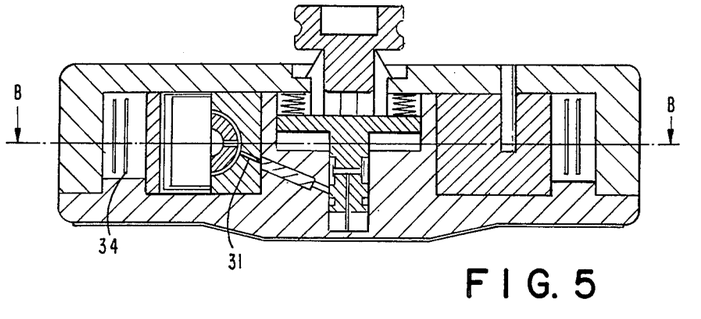
FIG. 5 is a cross-section (A—A) through another embodiment of the invention.
Figure 6:
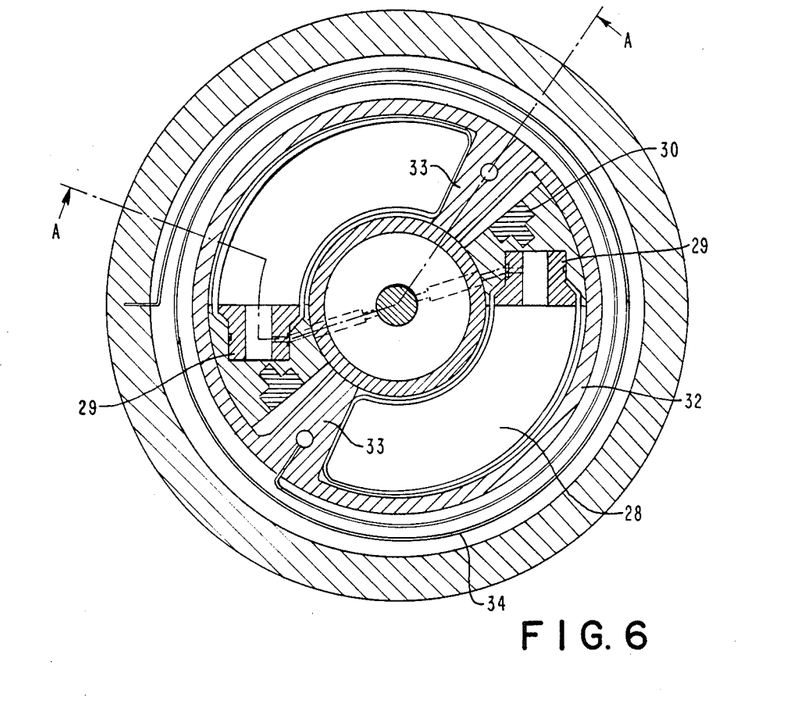
FIG. 6 is a section taken along plane B—B of FIG. 5.

In the embodiment shown in FIGS. 5 and 6 an alternative facility for conveying the active principle and a different form of reservoir is compressible and are provided. The reservoir is in the form squeezabled of two bags or bubbles or bellows 28 formed on one side with an aperture by which they are secured to a mount 29 formed with a filling aperture 30 and a bore or orifice 31 communicating with the central bore 9. The two mounts 29 are rigidly connected to the central cylindrical part of the casing bottom part 1. A rotating member 32 is disposed around this stationary part and has two inwardly projecting webs 33 each engaging with the backs of the bags 28.

Between the member 32 and the outside wall of the casing top part 2 is a compartment receiving a spiral spring 34. The same is secured at one end in the casing wall and at its other end in the member 32. When the spiral spring 34 expands, it rotates the member 32, the webs thereof compressing the bags 28 so that the active principle therein empties through the orifices 31.

By using just some of the usable number of turns of the spiral spring 34 to produce the rotary movements (e.g., limit the number of turns applied to the spring), a control effect is achieved. Consequently, the driving spring 34 is operative both to convey the active principle and to control its flow. In other respects this embodiment of FIGS. 5 and 6 operates similarly to the embodiment shown in FIGS. 1 and 2.

Figure 7:
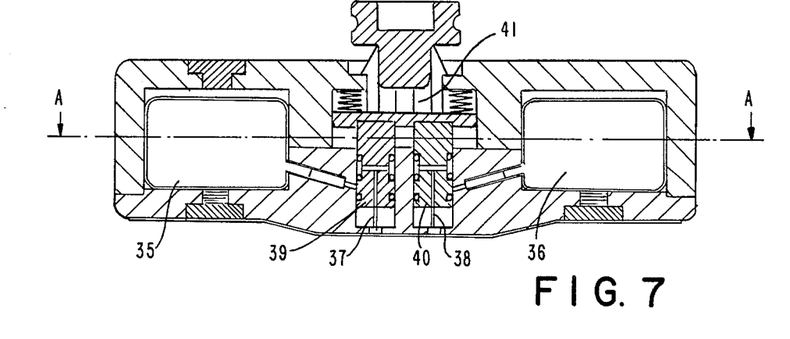
FIG. 7 is a cross-section through another embodiment of the invention.
Figure 8:
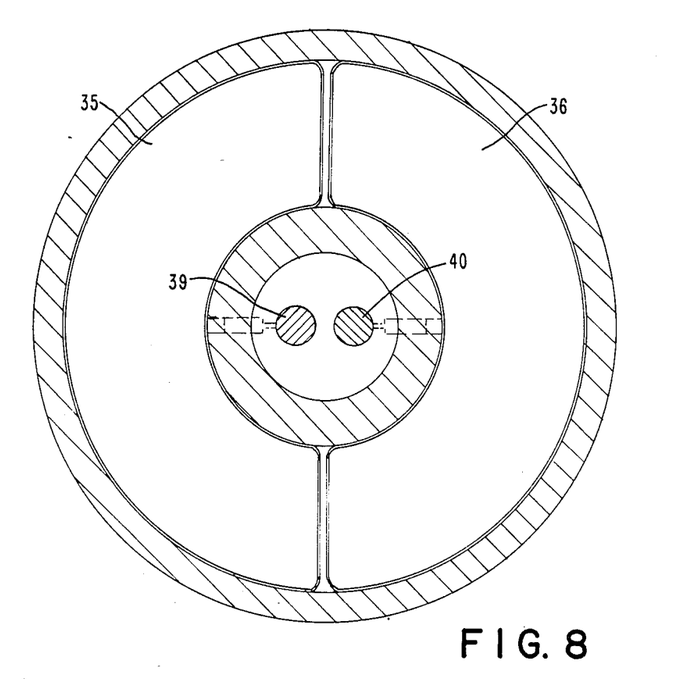
FIG. 8 is a section taken along plane A—A through the appliance of FIG. 7.

In contrast to the embodiments so far described, the appliance shown in FIGS. 7 and 8 has two supply vessels or chambers 35, 36 and two separate needle carrier 39, 40 which have needles 37, 38 and which a common activating mechanism 41 drives. This embodiment is of use when it is required to inject two active principles simultaneously and separately.

As an alternative to the version shown, a single needle carrier having two needles could be provided instead of the two needle carriers with two needles, in which event the sealing system would have to be more elaborate but within the contemplation of this invention.

Figure 9:
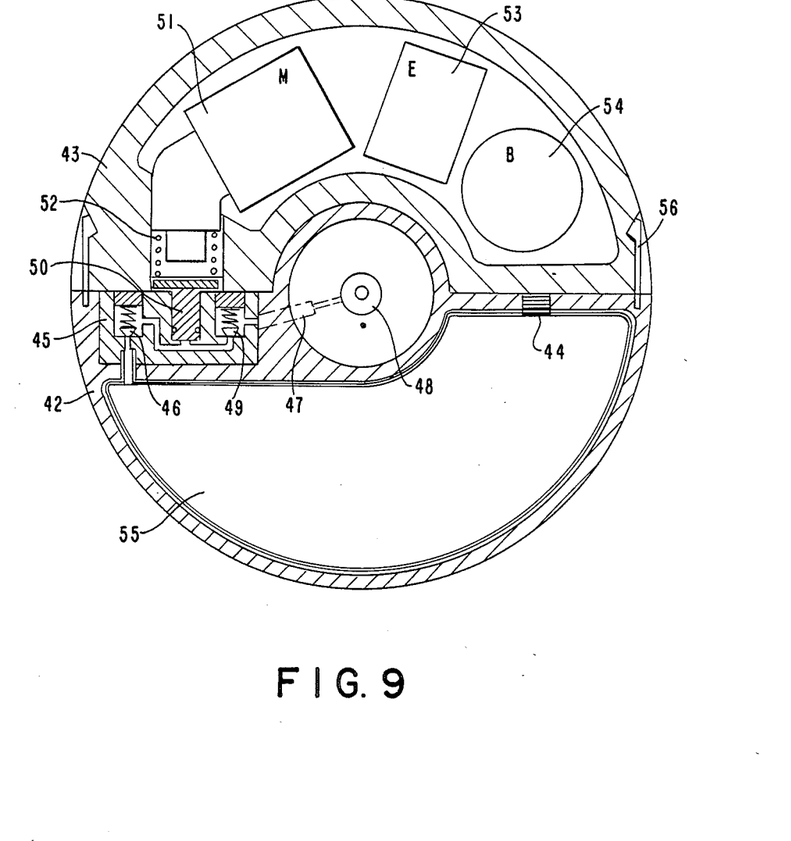
FIG. 9 is a section through another embodiment of the invention on a plane perpendicular to its axis.

The embodiment shown in section in FIG. 9 has electrically driven conveyance of the active principle. Because of the relatively high cost of the electrical elements of this embodiment the appliance is divided into a discardable part 42 and a reusable part 43. The two parts 42, 43 are interconnected by resilient clips 56 which engage in corresponding recesses.

The disposable part 42 comprises a supply vessel 55 with its provision for filling being closed by a partition 44. The system is such that the reservoir can, if required, be filled shortly before use. The disposable part 42 also comprises pump means 45 having an intake valve 46 communicating with the supply vessel 55, a delivery valve 49 controlling a line 47 to an injection needle 48, and a plunger pump 50 disposed between and connected to the two valves 46 and 49. The pump means 45 operate as follows: when the plunger of the pump 50 is drawn back from the position shown, a predetermined volume of active principle is intaken through the intake valve 46 from the supply vessel. The delivery valve 49 stays closed in this phase. When the piston makes its next advance, the intake valve 46 closes and the delivery valve 49 opens so that the intaken volume is supplied to the injection needle.

The injection needle 48 together with the needle carrier and the piercing mechanism (not shown here) also forms part of the discardable part.

The more valuable reusable part 43 contains the electric drive for the pump means, in the form of an electromagnet 51 which draws the plunger of the pump 50 back, the plunger being advanced by a return spring 52.

An electronic control facility 53 controls the electromagnet 51. A battery 54 provides power for the electromagnet 51 and the electronic control 53.

An electrically driven pump is particularly suitable for combination with the electronically controlling of the quantity of active principle to be released. The release profile can, for example, be pre-programmed and stored in some suitable way. The release rate can be checked by appropriate sensors.

In the embodiments shown, the needle-driving means have been combined with the operation of the valve. These two operations can readily be separated so that, for example, first the needle is shot, whereafter a valve opens separately. Skin-piercing movements other than simple injection perpendicularly to the skin surface are possible; for example, the vertical piercing movement can be coupled with rotation of the needle, or the needle can be injected into the skin at an inclination to the skin surface.

While the invention has been described in conjunction with certain embodiments, it is understood that various modifications and changes may be made without departing from the spirit and scope of the invention.

We claim:

1. A portable appliance for subcutaneous or intradermal injection of a liquid formulation of an active principle into a patient comprising:
   a housing having a patient engaging surface to contact a patient's skin;
   a supply vessel positioned within said housing for storing the liquid formulation;
   infusion needle means having an infusion needle and positioned in said housing, said means used for establishing communication between said supply vessel and said infusion needle when said infusion needle is activated to advance into the patient's skin a preselected distance;
   pump means for emptying the liquid formulation from said supply vessel through said infusion needle means;
   needle driving means for subcutaneous or intradermal injection of the infusion needle through the patient engaging surface and into the patient's skin through an injection site the preselected distance; and
   securing means for securing the patient engaging surface of the appliance to a portion of the patient's skin substantially surrounding the injection site through which the infusion needle enters the patient's skin thereby providing a tight adherence of the patient engaging surface to the patient's skin.

2. The apliance of claim 30 wherein said injection needle means further comprises: flow control means for controlling the flow of the liquid formulation through the injection needle.

3. The appliance of claim 1, wherein the supply vessel is in the form of a plunger syringe having a cylinder which is operative as supply vessel.

4. The appliance of claim 1, having at least one additional supply vessel.

5. The appliance of claim 1, wherein the pump means comprise a mechanical drive.

6. The appliance of claim 5, wherein the mechanical drive comprises a spring.

7. The appliance of claim 6, wherein only a fraction of a spring deflection of a driving spring is used.

8. The appliance of claim 5 wherein the mechanical drive comprises a memory alloy.

9. The appliance of claim 5 wherein the mechanical drive comprises a clockwork drive.

10. The appliance of claim 1, wherein the securing means is in the form of an adhesive layer.

11. The appliance of claim 10, wherein the advesive layer contains a local anesthetic.

12. The appliance of claim 1, wherein the securing means comprise a plaster.

13. The appliance of claim 1, wherein the injection has a diameter of less than about 0.05 mm.

14. The appliance of claim 1, wherein the needle-driving means is combined with a valve controlling communication between the supply vessel and the needle.

15. The appliance of claim 1, wherein electronic control means for controlling the pump means are provided, the control means having a data memory for a programmed release profile.

16. The appliance of claim 1, wherein the pump means is in the form of a squeezable hose pump which is of variable hose cross-section and which enables the release profile to be programmed.

17. The appliance of claim 1, wherein the needle-driving means are designed for a penetration depth of from about 0.5 to about 5 mm.

18. The appliance of claim 1, further comprising sensor means to control or vary the release rate of formulation.

19. The appliance of claim 1 wherein the supply vessel is a supply chamber of the appliance.

20. The appliance of claim 19 wherein the pump means comprises a diaphragm separating the supply chamber into two subchambers.

21. The appliance of claim 1 wherein the pump means further comprises a pump chamber separated from said supply vessel by a resilient diaphragm; and pressure producing means positioned in said pump chamber for producing a preselected pressure to empty said supply vessel of said liquid formulation.

22. The appliance according to claim 21, wherein the pump chamber is filled with a propellant vapour.

23. The appliance according to claim 21 wherein the pressure producing means comprises an electrochemical pressure producing device.

24. The appliance according to claim 23, wherein said electrochemical pressure producing device is an electro-osmtic or osmotic pump.

25. The appliance according to claim 21 wherein said pressure producing means further comprises: a device having photochemical means for producing pressure to empty the liquid formulation from said supply vessel using a photochemical reaction.

26. The appliance according to claim 21 wherein said pressure-producing means further comprises: a device having chemical means for producing pressure to empty the supply vessel using a chemical reaction.

27. The appliance according to claim 1, wherein the supply vessel defines a closable aperture used to fill said vessel; and a partition means for closing said aperture.

28. The appliance according to claim 1 wherein the housing is divided into a reusable part and a discardable part, the reusable part comprising driving means for driving the pump means.

29. The appliance according to claim 28, wherein the discardable part comprises the supply vessel, the infusion needle means, the pump means and the needle driving means.

30. The appliance of claim 1 wherein the supply vessel is a compressible reservoir.

31. The appliance of claim 30 wherein the compressible reservoir is in the form of a bellows.

32. The appliance of claim 31, further comprising an absorbent material which is provided in the supply vessel to take up the active principle.

33. The appliance of claim 1 wherein the pump means comprises an electic drive.

34. The appliance of claim 33 wherein the electric drive is an electric pump.

35. The appliance of claim 34 wherein the electric drive is a piezoelectric pump.

36. The appliance of claim 34 wherein the electric drive is a diaphragm pump.

37. The appliance of claim 1 wherein the pump means comprises a magnetic drive.

* * * * *